US012318535B2

(12) United States Patent
Sears et al.

(10) Patent No.: US 12,318,535 B2
(45) Date of Patent: *Jun. 3, 2025

(54) AEROSOL DELIVERY DEVICE WITH MICROFLUIDIC DELIVERY COMPONENT

(71) Applicant: RAI Strategic Holdings, Inc., Winston-Salem, NC (US)

(72) Inventors: Stephen Benson Sears, Siler City, NC (US); Michael F. Davis, Clemmons, NC (US); Karen V. Taluskie, Winston-Salem, NC (US); Yi-ping Chang, Greensboro, NC (US); Eric Taylor Hunt, Pfafftown, NC (US); Andries Don Sebastian, Winston-Salem, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 885 days.

This patent is subject to a terminal disclaimer.

(21) Appl. No.: 17/495,525

(22) Filed: Oct. 6, 2021

(65) Prior Publication Data
US 2022/0023555 A1    Jan. 27, 2022

Related U.S. Application Data

(63) Continuation of application No. 16/217,784, filed on Dec. 12, 2018, now Pat. No. 11,160,939, which is a
(Continued)

(51) Int. Cl.
*A61M 15/06* (2006.01)
*A24F 40/30* (2020.01)
(Continued)

(52) U.S. Cl.
CPC ............. *A61M 15/06* (2013.01); *A24F 40/30* (2020.01); *A24F 40/485* (2020.01);
(Continued)

(58) Field of Classification Search
CPC ........ A24F 40/10; A24F 40/30; A24F 40/485; A61M 11/042; A61M 15/06;
(Continued)

(56) References Cited

U.S. PATENT DOCUMENTS

| 1,771,366 A | 7/1930 | Wyss et al. |
| 2,057,353 A | 10/1936 | Whittemore. , Jr. |

(Continued)

FOREIGN PATENT DOCUMENTS

| AU | 276250 | 7/1965 |
| CA | 2 641 869 | 5/2010 |

(Continued)

*Primary Examiner* — Sang Y Paik
(74) *Attorney, Agent, or Firm* — Womble Bond Dickinson (US) LLP

(57) ABSTRACT

The present disclosure relates to a microfluidic vaporizer, an aerosol delivery device that may include such vaporizer, and methods for forming an aerosol. A microfluidic vaporizer can comprise a substrate that defines: a reservoir configured to hold a liquid; a heater adapted to vaporize the liquid; and a capillary channel configured for movement of the liquid from the reservoir to the heater. An aerosol delivery device can comprise a shell and a microfluidic vaporizer. The microfluidic vaporizer and aerosol delivery device can be used for forming aerosols with precise and reproducible compositions.

21 Claims, 7 Drawing Sheets

Related U.S. Application Data continuation of application No. 14/643,626, filed on Mar. 10, 2015, now Pat. No. 10,172,388.

(51) Int. Cl.
*A24F 40/485* (2020.01)
*A61M 11/04* (2006.01)
*B01F 23/213* (2022.01)
*A24F 40/10* (2020.01)

(52) U.S. Cl.
CPC ....... *A61M 11/042* (2014.02); *B01F 23/2133* (2022.01); *A24F 40/10* (2020.01); *A61M 2205/3653* (2013.01); *A61M 2205/8206* (2013.01)

(58) Field of Classification Search
CPC ... A61M 2205/3653; A61M 2205/8206; B01F 23/2133
USPC ......................................................... 392/387
See application file for complete search history.

(56) References Cited

U.S. PATENT DOCUMENTS

| | | |
|---|---|---|
| 2,104,266 A | 1/1938 | McCormick |
| 3,200,819 A | 8/1965 | Gilbert |
| 4,284,089 A | 8/1981 | Ray |
| 4,303,083 A | 12/1981 | Burruss, Jr. |
| 4,735,217 A | 4/1988 | Gerth et al. |
| 4,848,374 A | 7/1989 | Chard et al. |
| 4,907,606 A | 3/1990 | Lilja et al. |
| 4,922,901 A | 5/1990 | Brooks et al. |
| 4,945,931 A | 8/1990 | Gori |
| 4,947,874 A | 8/1990 | Brooks et al. |
| 4,947,875 A | 8/1990 | Brooks et al. |
| 4,986,286 A | 1/1991 | Roberts et al. |
| 5,019,122 A | 5/1991 | Clearman et al. |
| 5,042,510 A | 8/1991 | Curtiss et al. |
| 5,060,671 A | 10/1991 | Counts et al. |
| 5,093,894 A | 3/1992 | Deevi et al. |
| 5,144,962 A | 9/1992 | Counts et al. |
| 5,249,586 A | 10/1993 | Morgan et al. |
| 5,261,424 A | 11/1993 | Sprinkel, Jr. |
| 5,322,075 A | 6/1994 | Deevi et al. |
| 5,353,813 A | 10/1994 | Deevi et al. |
| 5,369,723 A | 11/1994 | Counts et al. |
| 5,372,148 A | 12/1994 | McCafferty et al. |
| 5,388,574 A | 2/1995 | Ingebrethsen et al. |
| 5,408,574 A | 4/1995 | Deevi et al. |
| 5,468,936 A | 11/1995 | Deevi et al. |
| 5,498,850 A | 3/1996 | Das |
| 5,515,842 A | 5/1996 | Ramseyer et al. |
| 5,530,225 A | 6/1996 | Hajaligol |
| 5,564,442 A | 10/1996 | MacDonald et al. |
| 5,649,554 A | 7/1997 | Sprinkel et al. |
| 5,666,977 A | 9/1997 | Higgins et al. |
| 5,687,746 A | 11/1997 | Rose et al. |
| 5,726,421 A | 3/1998 | Fleischhauer et al. |
| 5,727,571 A | 3/1998 | Meiring et al. |
| 5,743,251 A | 4/1998 | Howell et al. |
| 5,799,663 A | 9/1998 | Gross et al. |
| 5,819,756 A | 10/1998 | Mielordt |
| 5,865,185 A | 2/1999 | Collins et al. |
| 5,865,186 A | 2/1999 | Volsey, II |
| 5,878,752 A | 3/1999 | Adams et al. |
| 5,894,841 A | 4/1999 | Voges |
| 5,934,289 A | 8/1999 | Watkins et al. |
| 5,954,979 A | 9/1999 | Counts et al. |
| 5,967,148 A | 10/1999 | Harris et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,125,853 A | 10/2000 | Susa et al. |
| 6,155,268 A | 12/2000 | Takeuchi |
| 6,164,287 A | 12/2000 | White |
| 6,196,218 B1 | 3/2001 | Voges |
| 6,196,219 B1 | 3/2001 | Hess et al. |
| 6,505,907 B2 | 1/2003 | Ishinaga |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,772,756 B2 | 8/2004 | Shayan |
| 6,803,545 B2 | 10/2004 | Blake et al. |
| 6,854,461 B2 | 2/2005 | Nichols |
| 6,854,470 B1 | 2/2005 | Pu |
| 7,117,867 B2 | 10/2006 | Cox et al. |
| 7,293,565 B2 | 11/2007 | Griffin et al. |
| 7,513,253 B2 | 4/2009 | Kobayashi et al. |
| 7,683,029 B2 | 3/2010 | Hindle et al. |
| 7,775,459 B2 | 8/2010 | Martens, III et al. |
| 7,832,410 B2 | 11/2010 | Hon |
| 7,845,359 B2 | 12/2010 | Montaser |
| 7,896,006 B2 | 3/2011 | Hamano et al. |
| 8,127,772 B2 | 3/2012 | Montaser |
| 8,314,591 B2 | 11/2012 | Terry et al. |
| 8,365,742 B2 | 2/2013 | Hon |
| 8,402,976 B2 | 3/2013 | Fernando et al. |
| 8,499,766 B1 | 8/2013 | Newton |
| 8,528,569 B1 | 9/2013 | Newton |
| 8,550,069 B2 | 10/2013 | Alelov |
| 8,558,147 B2 | 10/2013 | Greim et al. |
| 9,220,302 B2 | 12/2015 | DePiano et al. |
| 9,491,974 B2 | 11/2016 | DePiano et al. |
| 9,668,521 B2 | 6/2017 | Kucaj |
| 9,854,841 B2 | 1/2018 | Ampolini et al. |
| 10,172,388 B2 * | 1/2019 | Sears ................. B01F 23/2133 |
| 2002/0146242 A1 | 10/2002 | Vieira |
| 2003/0226837 A1 | 12/2003 | Blake et al. |
| 2004/0118401 A1 | 6/2004 | Smith et al. |
| 2004/0129280 A1 | 7/2004 | Woodson et al. |
| 2004/0200488 A1 | 10/2004 | Felter et al. |
| 2004/0226568 A1 | 11/2004 | Takeuchi et al. |
| 2005/0016550 A1 | 1/2005 | Katase |
| 2006/0016453 A1 | 1/2006 | Kim |
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2008/0085103 A1 | 4/2008 | Beland et al. |
| 2008/0092912 A1 | 4/2008 | Robinson et al. |
| 2008/0142010 A1 | 6/2008 | Weaver et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0095311 A1 | 4/2009 | Hon |
| 2009/0095312 A1 | 4/2009 | Herbrich et al. |
| 2009/0126745 A1 | 5/2009 | Hon |
| 2009/0139520 A1 | 6/2009 | Weaver et al. |
| 2009/0188490 A1 | 7/2009 | Hon |
| 2009/0230117 A1 | 9/2009 | Fernando et al. |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0031968 A1 | 2/2010 | Sheikh et al. |
| 2010/0043809 A1 | 2/2010 | Magnon |
| 2010/0083959 A1 | 4/2010 | Siller |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0175960 A1 | 7/2011 | Fukumoto |

(56) References Cited

U.S. PATENT DOCUMENTS

| | | |
|---|---|---|
| 2011/0265806 A1 | 11/2011 | Alarcon et al. |
| 2011/0290248 A1 | 12/2011 | Schennum |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0037041 A1 | 2/2013 | Worm et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0104916 A1 | 5/2013 | Bellinger et al. |
| 2013/0192619 A1 | 8/2013 | Tucker et al. |
| 2013/0213418 A1 | 8/2013 | Tucker et al. |
| 2013/0255702 A1 | 10/2013 | Griffith, Jr. et al. |
| 2013/0298905 A1 | 11/2013 | Levin et al. |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0261488 A1 | 1/2014 | Andersson et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0157583 A1 | 6/2014 | Ward et al. |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0345631 A1 | 11/2014 | Bowen et al. |
| 2014/0353856 A1 | 12/2014 | Dubief |
| 2015/0053217 A1 | 2/2015 | Steingraber et al. |
| 2016/0007652 A1 | 1/2016 | Taluskie et al. |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| EP | 2340729 | 7/2011 |
| GB | 2469850 | 11/2010 |
| JP | H1133097 | 2/1999 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2006/044072 | 4/2006 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/009706 | 1/2012 |
| WO | WO 2012/072762 | 6/2012 |
| WO | WO 2012/100523 | 8/2012 |
| WO | WO 2013/060784 | 5/2013 |
| WO | WO 2013/089551 | 6/2013 |
| WO | WO 2014/012894 | 1/2014 |

\* cited by examiner

AEROSOL DELIVERY DEVICE WITH MICROFLUIDIC DELIVERY COMPONENT

CROSS-REFERENCE TO RELATED APPLICATIONS

The present application is a continuation of U.S. patent application Ser. No. 16/217,784, filed Dec. 12, 2018, which is a continuation of U.S. patent application Ser. No. 14/643,626, filed Mar. 10, 2015, the disclosures of which are incorporated herein by reference in their entirety.

FIELD OF THE DISCLOSURE

The present disclosure relates to aerosol delivery devices such as smoking articles, and more particularly to aerosol delivery devices that may utilize electrically generated heat for the production of aerosol (e.g., smoking articles commonly referred to as electronic cigarettes). The smoking articles may be configured to heat an aerosol precursor, which may incorporate materials that may be made or derived from tobacco or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices, and heat generating sources set forth in the background art described in U.S. Pat. No. 7,726,320 to Robinson et al., U.S. Pat. Pub. No. 2013/0255702 to Griffith Jr. et al., and U.S. patent application Ser. No. 13/647,000 to Sears et al., filed Oct. 8, 2012, which are incorporated herein by reference in their entirety. See also, for example, the various types of smoking articles, aerosol delivery devices, and electrically powered heat generating sources referenced by brand name and commercial source in U.S. patent application Ser. No. 14/170,838 to Bless et al., filed Feb. 3, 2014, which is incorporated herein by reference in its entirety.

It would be desirable to provide a reservoir for an aerosol precursor composition for use in an aerosol delivery device, the reservoir being provided so as to improve formation of the aerosol delivery device. It would also be desirable to provide aerosol delivery devices that are prepared utilizing such reservoirs.

SUMMARY OF THE DISCLOSURE

The present disclosure relates to microfluidic devices that may be used in formation of vapor. Such microfluidic devices are particularly useful as vaporizers in aerosol delivery device. A microfluidic vaporizer as described herein can be beneficial in providing for precise control over aerosol composition, providing for reduced quantities of liquid that may be needed to form the desired number of aerosol puffs on the aerosol delivery device, and reducing the power consumption required to provide the aerosol. The present disclosure further relates to aerosol delivery devices that specifically may incorporate a microfluidic vaporizer as described herein as well as methods of vapor and aerosol formation, methods of making a microfluidic vaporizer, and methods of making aerosol delivery devices.

In some embodiments, the present disclosure provides a microfluidic vaporizer comprising a substrate that defines: a reservoir configured to hold a liquid; a heater adapted to vaporize the liquid; and a capillary channel configured for movement of the liquid from the reservoir to the heater. The microfluidic vaporizer may be further configured according to the following statements, any two or more of which may be combined.

The microfluidic vaporizer can further comprise a cover overlying the substrate. At least a portion of the cover can be vapor permeable and liquid impermeable.

The substrate of the microfluidic vaporizer can be adapted for passive transfer of the liquid from the reservoir to the heater through the capillary channel.

The microfluidic vaporizer can further comprise an active transport element selected from the group consisting of valves, pumps, heaters, electrical field formers, stimuli-responsive materials, and combinations thereof.

The liquid in the microfluidic vaporizer can be an aerosol precursor composition or a component thereof. The liquid can comprise one or more flavors. The one or more flavors can include nicotine, particularly tobacco derived nicotine. The liquid can comprise an aerosol former. The aerosol former can be selected from the group consisting of water, glycerol, propylene glycol, and combinations thereof.

The substrate of the microfluidic vaporizer can comprise a plurality of heaters.

The substrate of the microfluidic vaporizer can comprise a plurality of reservoirs.

The microfluidic vaporizer can comprise a first reservoir with an aerosol former and a second reservoir with one or more flavors. The first reservoir and the second reservoir can be in fluid communication with the heater via the capillary channel. The first reservoir can be in fluid communication with a first heater via a first capillary channel, and the second reservoir can be in fluid communication with a second heater via a second capillary channel. Alternatively, the first and second reservoirs may be in fluid communication with the same heater. Any number of reservoirs, capillary channels, and heaters can be used in any combination, and the relative numbers of each element present in a given embodiment can vary.

The substrate of the microfluidic vaporizer can further comprise one or more electrical connection pins.

The reservoir(s) and/or the capillary channel(s) defined by the substrate of the microfluidic vaporizer can be etched in the substrate. The reservoir(s) and/or the capillary channel(s) may be formed in the substrate by any further suitable method as further described herein.

The heater of the microfluidic vaporizer can underlie at least a portion of the capillary channel.

The microfluidic vaporizer can comprise a plurality of capillary channels. The plurality of capillary channels can extend radially from the substrate. The microfluidic vaporizer can comprise a plurality of heaters positioned at terminal ends of the capillary channels. The heaters can be substantially disc shaped or may have a further shape. Capillary channels can be formed in the heaters positioned at the terminal ends of the capillary channels.

The substrate of the microfluidic vaporizer can be substantially in the form of a chip. Such form factor may comprise the materials including, but not limited to, Si and $SiO_2$.

In some embodiments, the present disclosure provides an aerosol delivery device. The aerosol delivery device can comprise a shell and a microfluidic vaporizer according to any embodiment or combinations of embodiments described herein. The aerosol delivery device may be further configured according to the following statements, any two or more of which may be combined.

The aerosol delivery device can comprise a first shell comprising the microfluidic vaporizer and a second shell comprising a power source.

The aerosol delivery device can further comprise a mouthpiece.

The aerosol delivery device can further comprise a microcontroller.

The aerosol delivery device can comprise an input adapted for providing a control instruction to the microcontroller. The input can be a touchscreen. The input can be an APP or other computer program that is installed on a computer or handheld computing device, such as a smartphone or tablet. The input can comprise one or more pushbuttons.

In some embodiments, an aerosol delivery device can comprise: a shell; and a microfluidic vaporizer comprising: a substrate; one or a plurality of liquid flavor reservoirs formed in the substrate; one or a plurality of liquid flavors positioned in the liquid flavor reservoirs; one or a plurality of liquid aerosol former reservoirs formed in the substrate; a liquid aerosol former in the liquid aerosol former reservoir(s); one or a plurality of heaters; a plurality of capillary channels configured for movement of the liquid flavor(s) and the liquid aerosol former to the heater(s); and one or more electrical connections. The aerosol delivery device may be further configured according to the following statements, any two or more of which may be combined.

The aerosol delivery device can be configured such that the liquid flavors can include nicotine. The nicotine can be positioned in a first liquid flavor reservoir and at least one further liquid flavor can be positioned in a second liquid flavor reservoir.

The aerosol delivery device can comprise a plurality of heaters. The aerosol delivery device can be formed such that a first capillary channel can be configured for movement of the liquid aerosol former to a first heater, and a second capillary channel can be configured for movement of at least one of the liquid flavors to a second heater. In further embodiments, multiple capillaries can be configured for movement of different components of an aerosol precursor composition (or e-liquid) to the same heater.

The aerosol delivery device can be configured such that separate liquid flavors can be positioned in separate liquid flavor reservoirs.

The aerosol delivery device can further comprise a microcontroller. The aerosol delivery device can further comprise an input adapted for providing a control instruction to the microcontroller.

The aerosol delivery device can be configured such that the microfluidic vaporizer can further comprise a cover overlying the substrate. The aerosol delivery device can be configured such that at least a portion of the cover can be vapor permeable and liquid impermeable.

The aerosol delivery device can further comprise an active transport element selected from the group consisting of valves, pumps, heaters, electrical field formers, stimuli-responsive materials, and combinations thereof. The active transport element can be defined by the substrate or may be otherwise included in the shell and in active communication with the substrate so as to activate liquid transport in the substrate.

The aerosol delivery device can further comprise a container that is in fluid communication with the microfluidic vaporizer and that can include one or more aerosol precursor components that are retained by or within the container. The container may be positioned substantially orthogonal to the microfluidic reservoir.

In some embodiments, the present disclosure provides methods of forming an aerosol. As an exemplary embodiment, a method of forming an aerosol can comprise providing an aerosol delivery device according to any embodiment or combinations of embodiments described herein; delivering a control signal to a microfluidic vaporizer causing a defined aliquot of a liquid aerosol former and optionally a defined aliquot of at least one liquid flavor to move through one or more capillary channels to one or more heaters; and delivering a control signal to the microfluidic vaporizer causing the heater(s) to heat and vaporize the liquid aerosol former and any optional liquid flavors delivered to the heater(s).

BRIEF DESCRIPTION OF THE FIGURES

Figure 1:
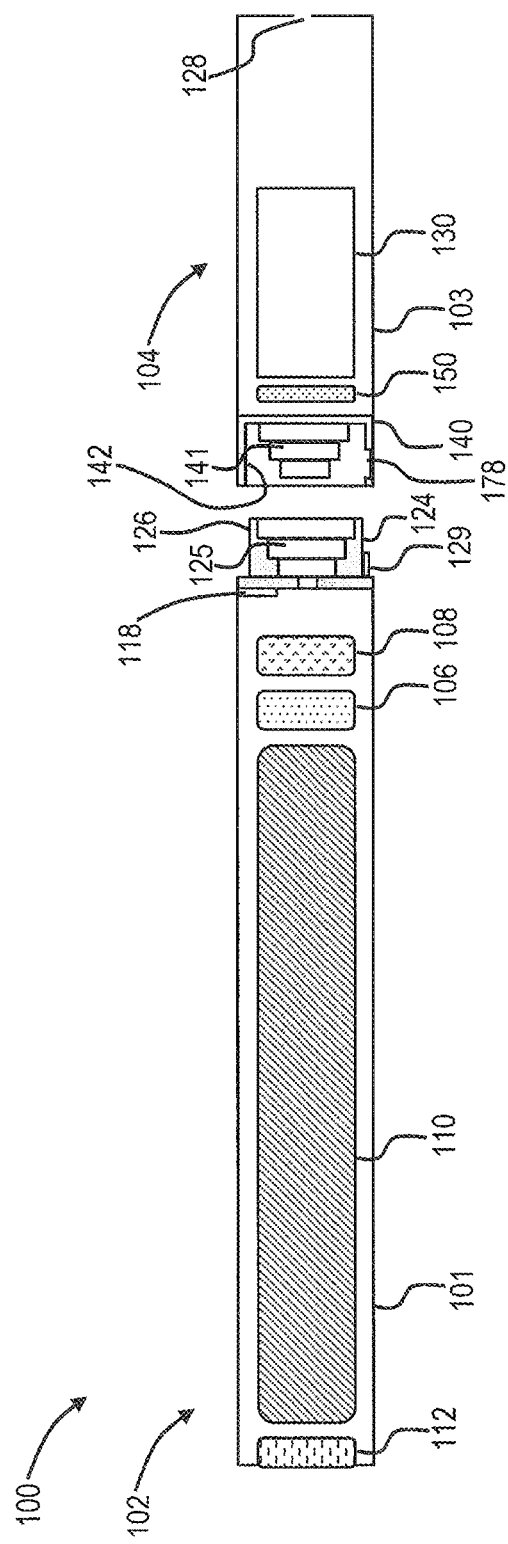
Figure 2:
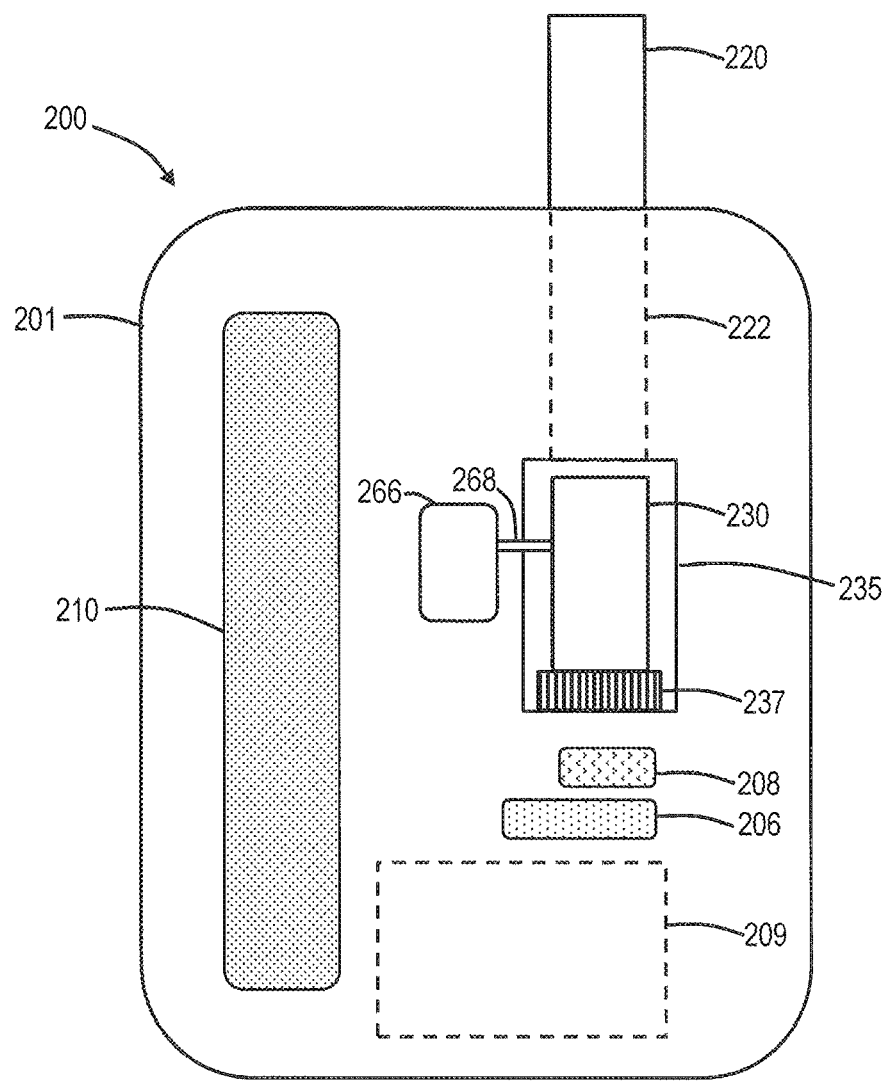
Figure 3:
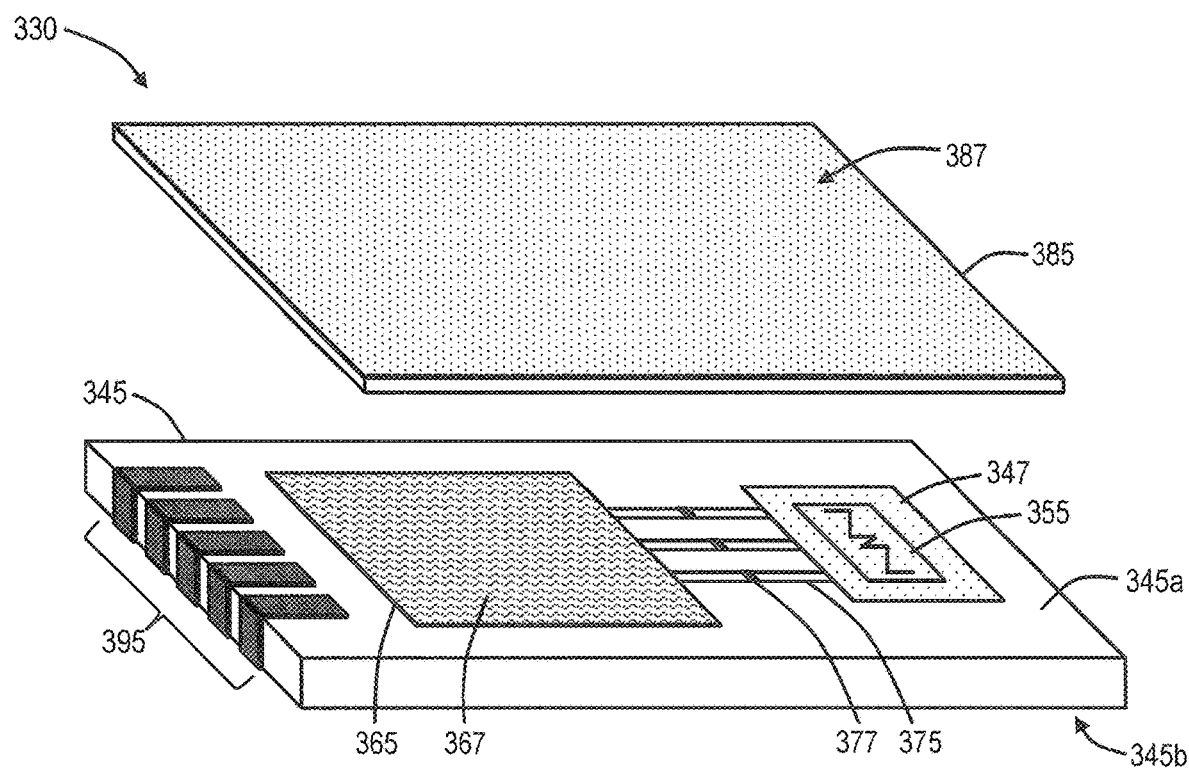
Figure 4:
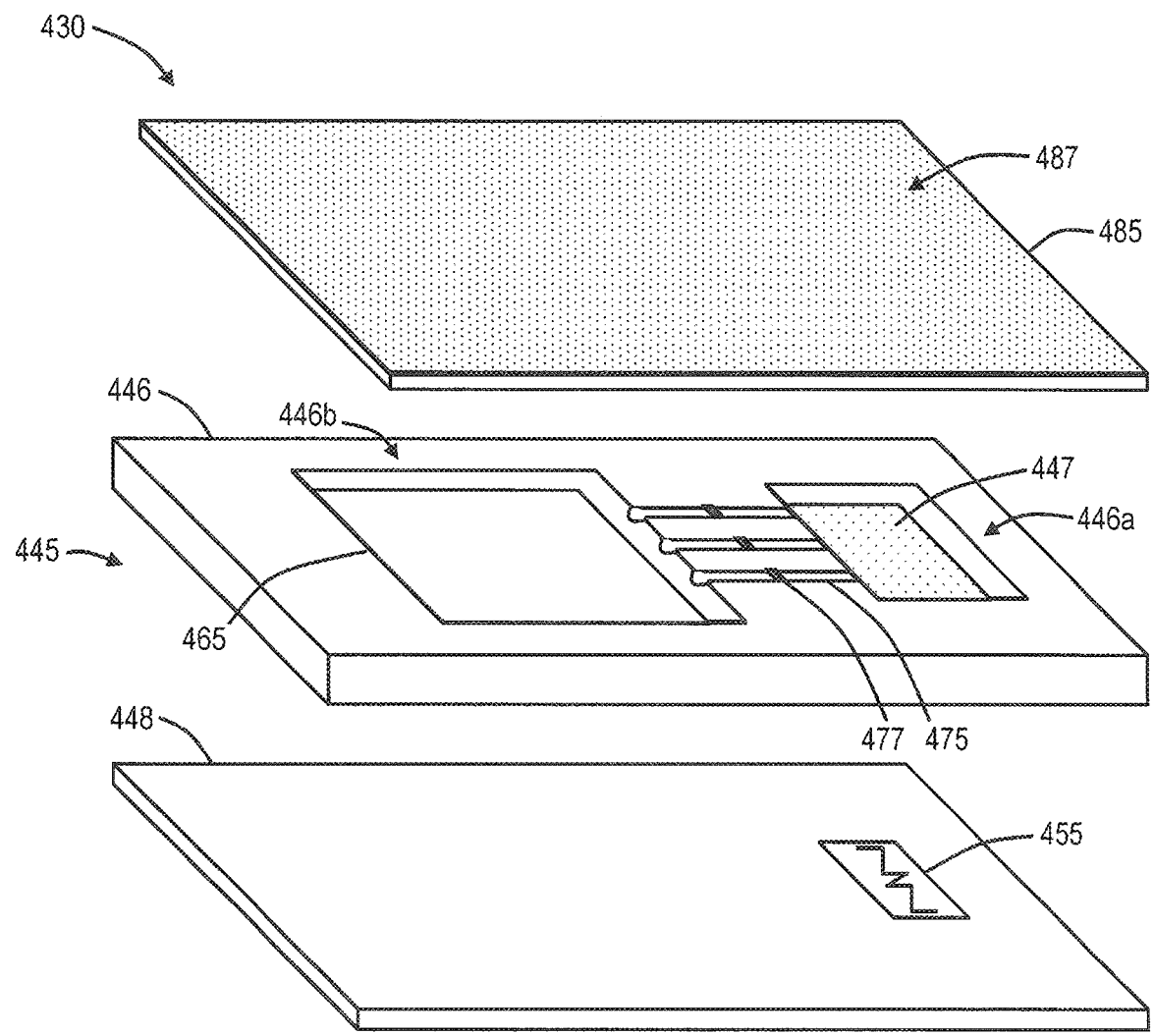
Figure 5:
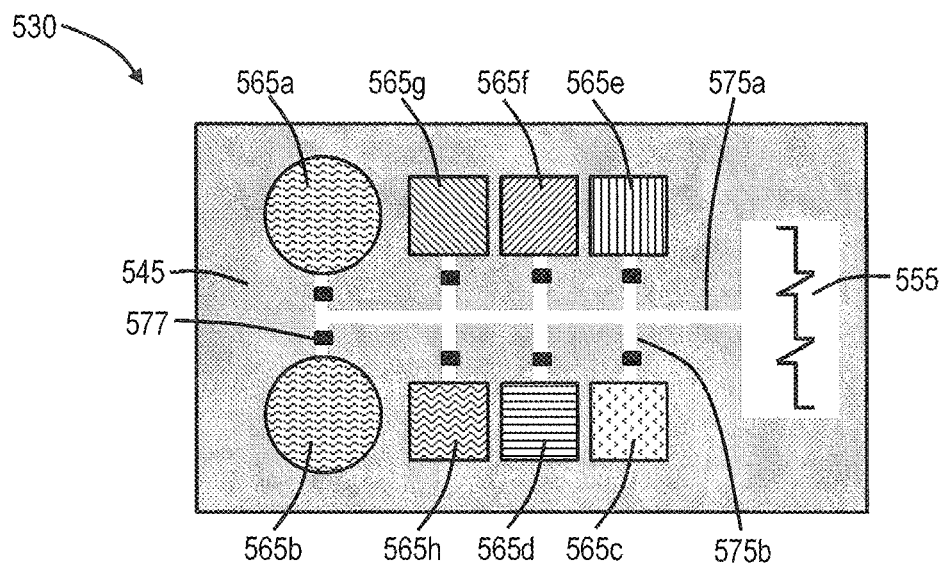
Figure 6:
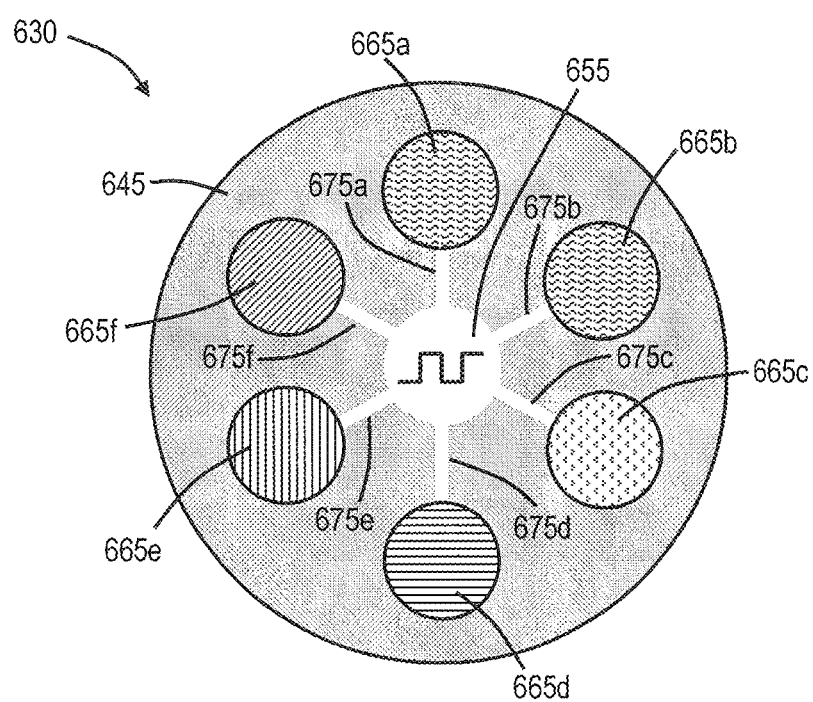
Figure 7:
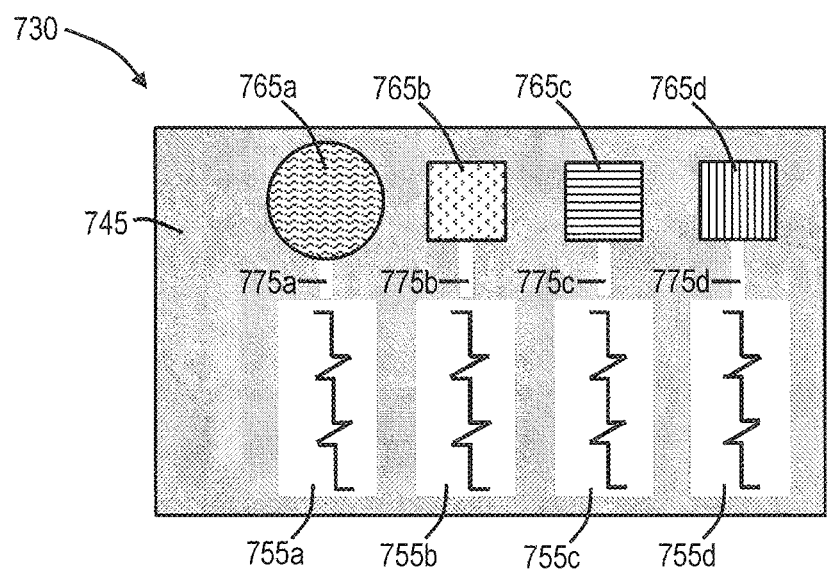
Figure 8:
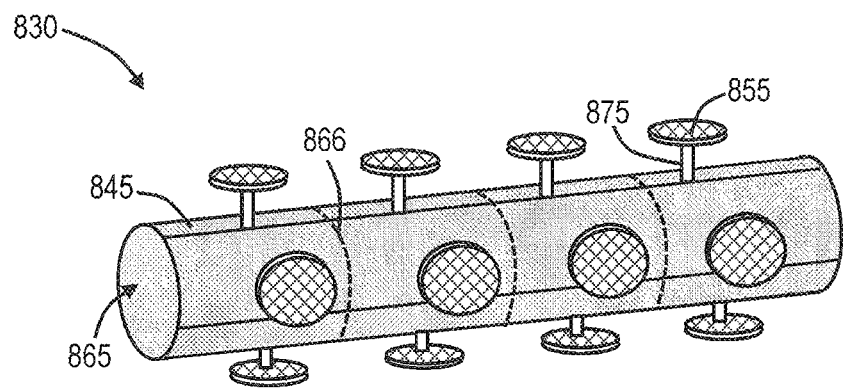
Figure 9:
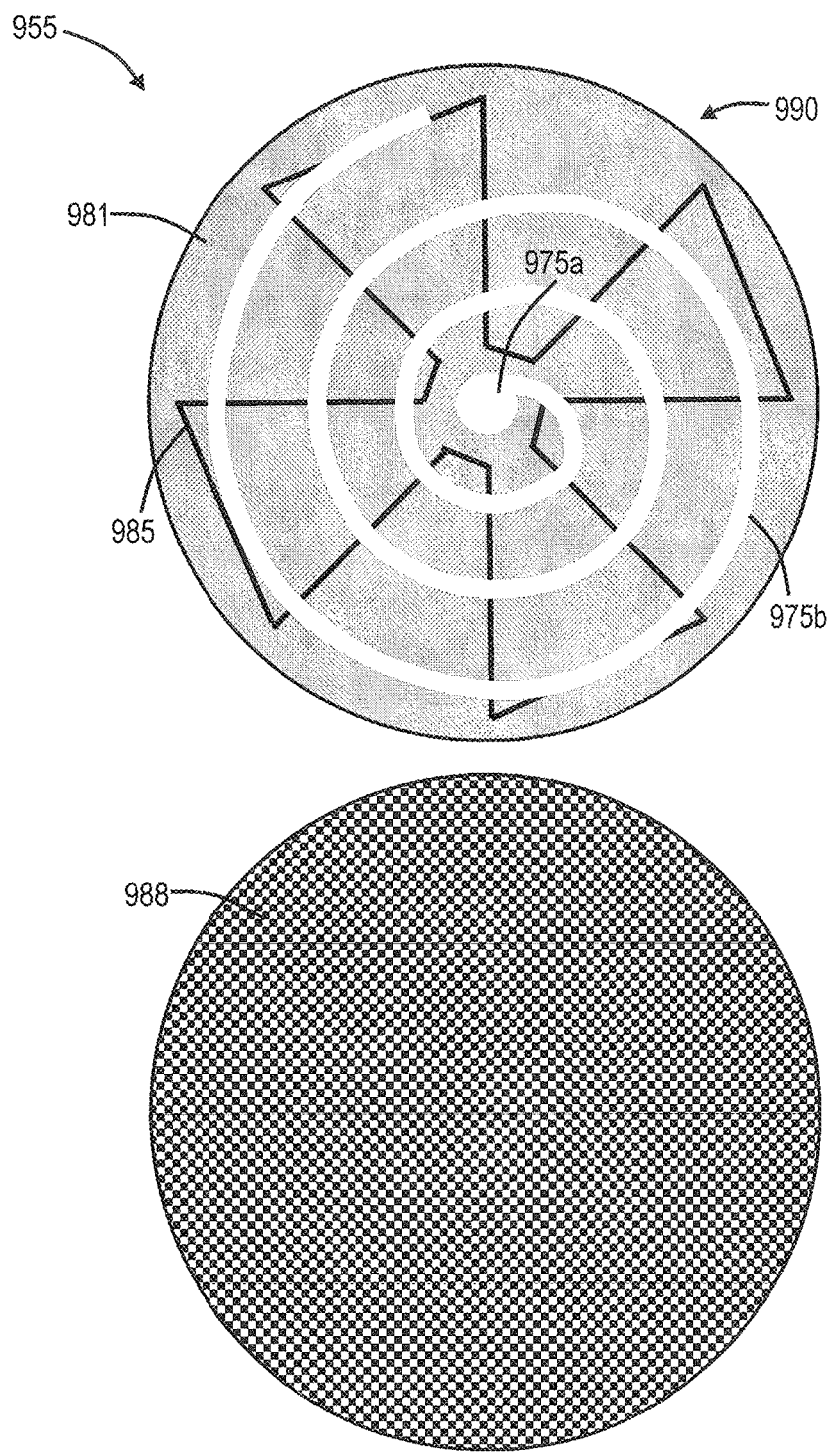

Having thus described the disclosure in the foregoing general terms, reference will now be made to the accompanying drawings, which are not necessarily drawn to scale, and wherein:

FIG. 1 is a partially cut-away view of an aerosol delivery device comprising a cartridge and a control body that includes a microfluidic vaporizer according to an example embodiment of the present disclosure;

FIG. 2 is a partially cut-away view of an aerosol delivery device comprising a shell with a mouthpiece and a microfluidic vaporizer according to an example embodiment of the present disclosure;

FIG. 3 is a partially exploded view of a microfluidic vaporizer according to an example embodiment of the present disclosure;

FIG. 4 is a partially exploded view of a further microfluidic vaporizer according to an example embodiment of the present disclosure;

FIG. 5 is a top view of a microfluidic vaporizer comprising a plurality of reservoirs according to an example embodiment of the present disclosure;

FIG. 6 is a top view of a microfluidic vaporizer comprising a plurality of reservoirs radially positioned around a single heater according to an example embodiment of the present disclosure;

FIG. 7 is a top view of a microfluidic vaporizer comprising a plurality of reservoirs and a plurality of dedicated heaters according to an example embodiment of the present disclosure;

FIG. 8 is a perspective view of a microfluidic reservoir comprising a reservoir with a plurality of capillary channels extending radially therefrom and having a plurality of heaters positioned at terminal ends thereof according to an example embodiment of the present disclosure;

FIG. 9 is a top view of a heater in a substantially disc shaped form that has a capillary channel overlying a heating element formed on a heater floor and having a heater cover (shown removed from the heater for clarity of view) that includes microperforations, the heater being according to an example embodiment of the present disclosure.

DETAILED DESCRIPTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As described hereinafter, embodiments of the present disclosure relate to aerosol delivery systems. Aerosol delivery systems according to the present disclosure use electrical energy to heat a material (preferably without combusting the material to any significant degree and/or without significant chemical alteration of the material) to form an inhalable substance; and components of such systems have the form of articles that most preferably are sufficiently compact to be considered hand-held devices. That is, use of components of preferred aerosol delivery systems does not result in the production of smoke—i.e., from by-products of combustion or pyrolysis of tobacco, but rather, use of those preferred systems results in the production of vapors resulting from volatilization or vaporization of certain components incorporated therein. In preferred embodiments, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

Aerosol delivery devices of the present disclosure generally include a number of components provided within an outer body or shell, which may be referred to as a housing. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary housing, or the elongated housing can be formed of two or more separable bodies. For example, an aerosol delivery device can comprise an elongated shell or body that can be substantially tubular in shape and, as such, resemble the shape of a conventional cigarette or cigar. In one embodiment, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., a rechargeable battery and various electronics for controlling the operation of that article), and at the other end and removably attached thereto an outer body or shell containing a disposable portion (e.g., a disposable cartridge include one or more aerosol precursor components, such as flavors and aerosol formers).

Aerosol delivery devices of the present disclosure can be formed of an outer housing or shell that is not substantially tubular in shape but may be formed to substantially greater dimensions. The housing or shell can be configured to include a mouthpiece and/or may be configured to receive a separate shell (e.g., a cartridge) that can include consumable elements, such as a liquid aerosol former, and can include a vaporizer.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microcontroller or microprocessor), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthpiece or mouth region for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure.

One example embodiment of an aerosol delivery device 100 according to the present disclosure is provided in FIG. 1. As seen in the cut-away view illustrated therein, the aerosol delivery device 100 can comprise a control body 102 and a cartridge 104 that can be permanently or detachably aligned in a functioning relationship. Engagement of the control body 102 and the cartridge 104 can be press fit (as illustrated), threaded, interference fit, magnetic, or the like. In particular, connection components, such as further described herein may be used. For example, the control body may include a coupler that is adapted to engage a connector on the cartridge.

In specific embodiments, one or both of the control body 102 and the cartridge 104 may be referred to as being disposable or as being reusable. For example, the control body may have a replaceable battery or a rechargeable battery and thus may be combined with any type of recharging technology, including connection to a typical electrical outlet, connection to a car charger (i.e., cigarette lighter receptacle), and connection to a computer, such as through a universal serial bus (USB) cable. For example, an adaptor including a USB connector at one end and a control body connector at an opposing end is disclosed in U.S. patent application Ser. No. 13/840,264 to Novak et al., filed Mar. 15, 2013, which is incorporated herein by reference in its entirety. Further, in some embodiments the cartridge may comprise a single-use cartridge, as disclosed in U.S. patent application Ser. No. 13/603,612 to Chang et al., filed Sep. 5, 2012, which is incorporated herein by reference in its entirety.

As illustrated in FIG. 1, a control body 102 can be formed of a control body shell 101 that can include a control component 106 (e.g., a microcontroller), a flow sensor 108, a battery 110, and an LED 112, and such components can be variably aligned. Further indicators (e.g., a haptic feedback component, an audio feedback component, or the like) can be included in addition to or as an alternative to the LED. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; and U.S. patent application Ser. No. 14/173,266, filed Feb. 5, 2014, to Sears et al.; which are incorporated herein by reference.

A cartridge 104 particularly can include a microfluidic vaporizer 130. Such vaporizer can take on a variety of configurations as otherwise described herein.

An opening 128 may be present in the cartridge shell 103 (e.g., at the mouthend) to allow for egress of formed aerosol from the cartridge 104. Such components are representative of the components that may be present in a cartridge and are not intended to limit the scope of cartridge components that are encompassed by the present disclosure.

The cartridge 104 also may include one or more electronic components 150, which may include an integrated circuit, a memory component, a sensor, or the like. The electronic component 150 may be adapted to communicate with the control component 106 and/or with an external device by wired or wireless means. The electronic component 150 may be positioned anywhere within the cartridge 104 or its base 140.

Although the control component 106 and the flow sensor 108 are illustrated separately, it is understood that the control component and the flow sensor may be combined as an electronic circuit board with the air flow sensor attached directly thereto. Further, the electronic circuit board may be positioned horizontally relative the illustration of FIG. 1 in that the electronic circuit board can be lengthwise parallel to the central axis of the control body. In some embodiments, the air flow sensor may comprise its own circuit board or other base element to which it can be attached.

The control body 102 and the cartridge 104 may include components adapted to facilitate a fluid engagement therebetween. As illustrated in FIG. 1, the control body 102 can include a coupler 124 having a cavity 125 therein. The cartridge 104 can include a base 140 adapted to engage the coupler 124 and can include a projection 141 adapted to fit within the cavity 125. Such engagement can facilitate a stable connection between the control body 102 and the cartridge 104 as well as establish an electrical connection between the battery 110 and control component 106 in the control body and the microfluidic vaporizer 130 in the cartridge. Further, the control body shell 101 can include an air intake 118, which may be a notch in the shell where it connects to the coupler 124 that allows for passage of ambient air around the coupler and into the shell where it then passes through the cavity 125 of the coupler and into the cartridge through the projection 141.

A coupler and a base useful according to the present disclosure are described in U.S. patent application Ser. No. 13/840,264 to Novak et al., filed Mar. 15, 2013, the disclosure of which is incorporated herein by reference in its entirety. For example, a coupler as seen in FIG. 1 may define an outer periphery 126 configured to mate with an inner periphery 142 of the base 140. In one embodiment the inner periphery of the base may define a radius that is substantially equal to, or slightly greater than, a radius of the outer periphery of the coupler. Further, the coupler 124 may define one or more protrusions 129 at the outer periphery 126 configured to engage one or more recesses 178 defined at the inner periphery of the base. However, various other embodiments of structures, shapes, and components may be employed to couple the base to the coupler. In some embodiments the connection between the base 140 of the cartridge 104 and the coupler 124 of the control body 102 may be substantially permanent, whereas in other embodiments the connection therebetween may be releasable such that, for example, the control body may be reused with one or more additional cartridges that may be disposable and/or refillable.

The aerosol delivery device 100 may be substantially rod-like or substantially tubular shaped or substantially cylindrically shaped in some embodiments. In other embodiments, further shapes and dimensions are encompassed— e.g., a rectangular or triangular cross-section, or the like.

In use, when a user draws on the article 100, airflow is detected by the sensor 108, the microfluidic vaporizer 130 is activated, and an aerosol precursor composition present within the microfluidic vaporizer is vaporized. Drawing upon the mouthend of the article 100 causes ambient air to enter the air intake 118 and pass through the cavity 125 in the coupler 124 and the central opening in the projection 141 of the base 140. In the cartridge 104, the drawn air combines with the formed vapor to form an aerosol. The aerosol is whisked away from the microfluidic vaporizer and out the mouth opening 128 in the mouthend of the article 100.

A further exemplary embodiment of an aerosol delivery device 200 according to the present disclosure is illustrated in the partial cross-section shown in FIG. 2. The aerosol delivery device 200 includes a shell 201 that is generally rectangular in shape but may take on any further shape that may be desired and is suitably sized to accommodate the further elements of the device. A battery 210, microcontroller 206, and sensor 208 are also present in the shell 201. The aerosol delivery device 200 in such embodiments can include a microfluidic vaporizer 230, which can be positioned within a vapor chamber 235. In particular, the microfluidic vaporizer 230 can include one or more electrical connection pins (not seen in FIG. 2) that allow for electrical attachment of the microfluidic vaporizer via a connection port 237. As such, the microfluidic vaporizer 230 can be detachable and replaceable. The aerosol delivery device 200 can include a mouthpiece 220 for passage of formed aerosol to a user of the device. The mouthpiece 220 may be fluidly connected to the vapor chamber (or directly to the microfluidic vaporizer) via an aerosol passage 222, and the mouthpiece can be retractable into the aerosol passage or into a further cavity or indentation in the aerosol delivery device 200.

As described further herein, a microfluidic vaporizer can comprise a substrate that defines at least one reservoir therein for containing one or more aerosol precursor components (or complete aerosol precursor compositions). In some embodiments, a reservoir may be provided in fluid connection to the microfluidic vaporizer and may be supplemental to any reservoir defined by the microfluidic vaporizer substrate. In other embodiments, a microfluidic vaporizer substrate may exclude a reservoir, and a separate reservoir may be provided in fluid connection with the microfluidic vaporizer. For example, as illustrated in FIG. 2, a container 266 is in fluid connection with the microfluidic vaporizer 230 via a liquid transport element 268. The container 266 may be in any form suitable for retaining a liquid component therein or thereby. For example, the container may be a bottle or other walled element having walls that are substantially impermeable to, and non-reactive with, any aerosol precursor components retained therein. As a further example, the container 266 may be a fibrous material in which liquid aerosol precursor components are absorbed, adsorbed, or otherwise stored therein or thereby. The liquid transport element 268 may be in any form suitable for transporting the liquid from the container 266 to the microfluidic vaporizer 230. For example, the liquid transport element 268 may be a wick that is fibrous, particulate, or otherwise suited for wicking of the liquid along the length thereof. In further embodiments, the liquid transport element 268 may be a capillary channel and thus may be substantially in the form of a flow tube that is appropriately sized for facilitating capillary action for movement of the liquid therethrough. In still further embodiments, the liquid transport element 268 may be sized so that capillary action is reduced or substantially absent, and liquid transport may be facilitated by one or more pumps or the like. Further, one or more valves may be present in the liquid transport element 268. The container 266 may be in any spatial arrangement with the microfluidic vaporizer 230. In certain embodiments, the container 266 can be substantially orthogonal to the microfluidic vaporizer 230. Further, a plurality of containers may be used. The liquid transport element 268 may transport the liquid directly to a heater or heating zone on the microfluidic vaporizer 230 and/or to a reservoir that is defined by the substrate of the microfluidic vaporizer (depending upon whether the container 266 is used instead of, or supplemental to, a reservoir that is defined by the microfluidic vaporizer substrate).

An input element may be included with the aerosol delivery device. To this end, a touchscreen 209 represented by dashed lines as optionally being present and accessible from an outer surface of the aerosol delivery device 200 is illustrated in FIG. 2. The touchscreen (or other input) may be included to allow a user to control functions of the device and/or for output of information to a user. Although a touchscreen 209 is illustrated in FIG. 2, the aerosol delivery device is not limited to a single embodiment. Rather, any component or combination of components may be utilized as an input for controlling the function of the device. For example, one or more pushbuttons may be used. As a further example, components adapted for gesture recognition based on specified movements of the aerosol delivery device may be used as an input. See U.S. patent application Ser. No. 14/565,137, filed Dec. 9, 2014, to Henry et al., which is incorporated herein by reference.

In some embodiments, an input may comprise a computer or computing device, such as a smartphone or tablet. In particular, the aerosol delivery device may be wired to the computer or other device, such as via use of a USB cord or similar protocol. The aerosol delivery device also may communicate with a computer or other device acting as an input via wireless communication. See, for example, the systems and methods for controlling a device via a read request as described in U.S. patent application Ser. No. 14/327,776, filed Jul. 10, 2014, to Ampolini et al., the disclosure of which is incorporated herein by reference. In such embodiments, an APP or other computer program may be used in connection with a computer or other computing device to input control instructions to the aerosol delivery device, such control instructions including, for example, the ability to form an aerosol of specific composition by choosing the nicotine content and/or content of further flavors to be included.

The various components of an aerosol delivery device according to the present disclosure can be chosen from components described in the art and commercially available. Examples of batteries that can be used according to the disclosure are described in U.S. Pat. App. Pub. No. 2010/0028766 to Peckerar et al., the disclosure of which is incorporated herein by reference in its entirety.

The aerosol delivery device can incorporate a sensor or detector for control of supply of electric power to the heat generation element when aerosol generation is desired (e.g., upon draw during use). As such, for example, there is provided a manner or method for turning off the power supply to the heat generation element when the aerosol delivery device is not being drawn upon during use, and for turning on the power supply to actuate or trigger the generation of heat by the heat generation element during draw. Additional representative types of sensing or detection mechanisms, structure and configuration thereof, components thereof, and general methods of operation thereof, are described in U.S. Pat. No. 5,261,424 to Sprinkel, Jr.; U.S. Pat. No. 5,372,148 to McCafferty et al.; and PCT WO 2010/003480 by Flick; which are incorporated herein by reference.

The aerosol delivery device most preferably incorporates a control mechanism for controlling the amount of electric power to the heat generation element during draw. Representative types of electronic components, structure and configuration thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. Pub. Nos. 2009/0230117 to Fernando et al. and 2014/0060554 to Collett et al.; and U.S. patent application Ser. No. 13/837,542, filed Mar. 15, 2013, to Ampolini et al. and Ser. No. 14/209,191, filed Mar. 13, 2014, to Henry et al.; which are incorporated herein by reference.

In various embodiments, the present disclosure is particularly beneficial in that the use of a microfluidic vaporizer in an aerosol delivery device can make it possible to precisely transport (and distribute) a desirable quantity of a liquid aerosol precursor to a heating zone. Many conventional aerosol delivery devices (e.g., electronic cigarettes) utilize combinations of a fibrous wick and a resistive heating coil to form a vapor by spontaneously wicking a liquid from a reservoir (typically a fibrous mat) via the fibrous wick to the resistive heating coil. As the liquid is vaporized by the resistive heating coil, more liquid spontaneously wicks from the reservoir to the heater. Such devices suffer from imprecise control of vapor formation—i.e., the inability to transport a single puff's worth of aerosol precursor to the heating zone at the desired time. Such devices likewise suffer from the inability to dispense only the precise amount of energy needed to vaporize the aerosol precursor liquid in a rapid fashion to provide aerosol on demand and avoid unnecessary energy drain on the battery.

A microfluidic vaporizer according to embodiments of the present disclosure can provide precision in vapor formation that is lacking in known devices. As used herein, the term microfluidic is intended to relate to the transfer of small volumes of liquid, such as milliliter or smaller, microliter or smaller, nanoliter or smaller, or picoliter or smaller. The ability to move liquid from a reservoir to a heater in small, precise volumes can provide for improving vapor formation as well as reducing unnecessary power drain.

In some embodiments, a microfluidic vaporizer can comprise a substrate that defines the specific components of the vaporizer. In particular, the substrate can define a reservoir that is configured to hold a liquid (e.g., an aerosol precursor composition or components thereof), a heater adapted to vaporize the liquid, and a capillary channel configured for movement of the liquid from the reservoir to the heater. The substrate can be formed of any material that is sufficiently inert in relation to the liquid and the level of heating necessary for vaporization. Specifically, the substrate is preferably chemically non-reactive with the components of the aerosol precursor composition (including aerosol formers, flavors, and the like). The substrate also is preferably thermally and mechanically stable under the conditions of use. For example, the substrate may be formed of a material that is temperature stable at a temperature of about 100° C. or greater, about 150° C. or greater, about 200° C. or greater, about 300° C. or greater, about 400° C. or greater, or about 500° C. or greater. In other embodiments, the supporting layer can be temperature stable in a temperature range of about 100° C. to about 750° C., about 125° C. to about to about 650° C., or about 150° C. to about 500° C. In some embodiments, the supporting layer can be formed of a ceramic material, particularly a silicon-based material. One specific example of a supporting layer material is a silicon nitride material. Other materials, however, such as glass or quartz can be used. Certain thermoplastic materials, such as cyclic olefin copolymers (COC), also can be used.

The substrate can take on a variety of shapes. In some embodiments, the substrate can be substantially chip shaped, but such shape is not required. The term chip shaped is intended to reference a shape that is substantially flat and has a length and a width that are both greater than the thickness. A chip shaped substrate may be substantially square or rectangular; however, other shapes (e.g., round, oval, triangle, or other multi-sided shapes) may also be considered chip shaped when substantially flat. In light of such exemplary shape, a microfluidic vaporizer can, in some embodiments, be characterized as a "lab-on-a-chip." Thus, a plurality of elements required for vaporization of a liquid can be included with the substrate. In some embodiments, the substrate can have a relatively small thickness—e.g., about 1 mm to about 20 mm, about 1.5 mm to about 15 mm, or about 2 mm to about 10 mm. In some embodiments, the substrate can have a surface area of about 0.5 $cm^2$ to about 50 $cm^2$, about 1 $cm^2$ to about 45 $cm^2$, about 2 $cm^2$ to about 40 $cm^2$, or about 3 $cm^2$ to about 30 $cm^2$.

One embodiment of a microfluidic vaporizer 330 is illustrated in FIG. 3. In the illustrated embodiment, the microfluidic vaporizer 330 comprises a substrate 345 that is substantially chip shaped. A heater 355 is defined by the substrate 345 and may be positioned on the substrate in a variety of manners. For example, the heater 355 may be on the top surface 345a of the substrate 345 or on the bottom surface 345b of the substrate. When on the bottom surface 345b of the substrate 345, the substrate preferably is sufficiently heat conductive to achieve vaporization of the liquid. In some embodiments, the heater 355 may be embedded in the substrate 345, such as being positioned within a well or other indentation in the substrate. In the illustrated embodiment, the heater 355 is positioned within a well formed in the substrate 345 and is covered by a heat conductive layer 347 (which is illustrated as being partially transparent in FIG. 3 to allow viewing of the heater 355 positioned under the heat conductive layer).

In some embodiments, the heater 355 may be characterized as a microheater. In particular, the microheater can be characterized as a Micro-Electro-Mechanical Systems (MEMS) based heater. MEMS-based heaters have been used previously in subminiature micro-sensors such as wind sensors, humidity sensors, and gas sensors. Such MEMS-based microheaters can emit heat by applying an electrical current to a resistor and can provide advantages such as low power input requirement and very short response time. A MEMS-based microheater is highly advantageous in a microfluidic vaporizer, as presently described, since it can provide for low voltage and/or low power device function while also providing rapid heating to a sufficiently high heat range to vaporize the liquid aerosol precursor composition.

A microheater useful herein may be described as a thin film heater or a hot film heater. This can be particularly descriptive of the physical nature of the microheater, which can comprise an electrically conductive material that specifically can be provided in the form of a film—i.e., an electrically conductive layer. In certain embodiments, the electrically conductive material can be patterned. In other words, the electrically conductive material can be present in the microheater in a specific pattern and, as such, refers to the physical nature of the finished microheater and is not limited to a method of making the microheater. The thickness of the electrically conductive layer can vary and can be, for example, about 1,000 µm or less, about 500 µm or less, about 200 µm or less, about 100 µm or less, about 50 µm or less, about 10 µm or less, or about 5 µm or less. In other embodiments, the electrically conductive layer can have a thickness of about 0.1 µm to about 500 µm, about 0.5 µm to about 200 µm, about 1 µm to about 100 µm, or about 2 µm to about 50 µm.

The electrically conductive material used in the microheater can comprise essentially any material that is both electrically conductive and suitable for thin film formation in the size ranges discussed above. For example, the electrically conductive material can be selected from the group consisting of elemental metals, metal alloys, silicon (including single crystal silicon and poly-silicon), ceramics, carbon, carbides, nitrides, and combinations thereof. In more specific embodiments, the electrically conductive material can be formed of platinum, gold, silver, copper, aluminum, tungsten, zinc, palladium, nickel, titanium, nichrome, silicon carbide, poly-silicon, single crystal silicon, titanium nitride, and the like. In particular embodiments, elemental metals, such as platinum, can be particularly beneficial due to exhibiting good oxidation resistance and long-term stability. A thin film microheater according to the present disclosure can exhibit a high level of ruggedness and stability that can be preferred over more fragile and less stable hot wires.

The use of a microheater in the microfluidic vaporizer can be particularly beneficial in that, in some embodiments, the material used in forming at least the microheater portion of the microfluidic vaporizer may be (or have properties consistent with) a semiconductor. As such, the semiconductor used in forming a microheater can be doped in a manner that modulates or tunes its electrical properties in a preferential manner.

In addition to the electrically conductive layer, a microheater according to the present disclosure can comprise a supporting layer. In particular, the electrically conductive material may be patterned on such supporting layer. The supporting layer preferably is formed of a material that is temperature stable under the heater operating temperatures. For example, the supporting layer can be temperature stable at a temperature of about 150° C. or greater, about 200° C. or greater, about 300° C. or greater, about 400° C. or greater, or about 500° C. or greater. In other embodiments, the supporting layer can be temperature stable in a temperature range of about 125° C. to about 750° C., about 150° C. to about to about 650° C., or about 175° C. to about 500° C. In some embodiments, the supporting layer can be formed of a ceramic material, particularly a silicon-based material. One specific example of a supporting layer material is a silicon nitride material. Other materials, however, such as glass or quartz can be used. Certain thermoplastic materials, such as cyclic olefin copolymers (COC), also can be used. The supporting layer can be formed of an insulating material or can include an insulating layer. Exemplary microheaters that may useful according to the present disclosure are described in U.S. Pat. No. 8,881,737 to Collett et al., which is incorporated herein by reference.

The heat conductive layer 347 preferably is formed of a material such that the heat conductive layer is temperature stable under the operating temperatures for the heater and that is heat radiant and/or heat conductive. For example, the heat conductive layer 347 can be temperature stable at a temperature of about 100° C. or greater, about 150° C. or greater, about 200° C. or greater, about 400° C. or greater, or about 500° C. or greater. In other embodiments, the heat conductive layer can be temperature stable in a temperature range of about 100° C. to about 750° C., about 150° C. to about to about 650° C., or about 175° C. to about 500° C. In some embodiments, the heat conductive layer can be in direct contact with an aerosol precursor composition or component thereof. Accordingly, it is preferable for the heat conductive layer to be substantially chemically non-reactive with the various compounds that may be included in the aerosol precursor material. By substantially chemically non-reactive is meant that any chemical reaction between the heat conductive layer and a component of the aerosol precursor material is sufficiently limited such that the heat conductive layer is not breached so as to allow the aerosol precursor composition to be in direct contact with the electrically conductive layer of the heater. Alternately, the phrase can mean that any chemical reaction between the heat conductive layer and a component of the aerosol precursor material is sufficiently limited such that chemical compounds present in the heat conductive layer are not released (or new chemical compounds formed) so as to combine with the formed aerosol for inhalation by a consumer. In some embodiments, the heat conductive layer can be formed of a ceramic material, particularly a silicon-based material. One specific example of a heat conductive layer material is a silicon dioxide material. Other materials, however, such as glass or quartz can be used.

The substrate 345 of the microfluidic vaporizer 330 illustrated in FIG. 3 further can include a reservoir 365 that is configured to hold an aerosol precursor composition 367 (or an element thereof). The reservoir particularly can be a well or other indentation formed in the substrate 345. In other embodiments, the microfluidic vaporizer 330 may have a multi-layer construction (see FIG. 4).

Although only a single reservoir is illustrated in FIG. 3, it is understood that a plurality of reservoirs may be included. Moreover, liquids for aerosolization may be separately stored in the plurality of reservoirs.

The aerosol precursor, or vapor precursor composition, can vary. Most preferably, the aerosol precursor is composed of a combination or mixture of various ingredients or components. The selection of the particular aerosol precursor components, and the relative amounts of those components used, may be altered in order to control the overall chemical composition of the mainstream aerosol produced by the aerosol generating piece. Of particular interest are aerosol precursors that can be characterized as being generally liquid in nature. For example, representative generally liquid aerosol precursors may have the form of liquid solutions, mixtures of miscible components, or liquids incorporating suspended or dispersed components. Typical aerosol precursors are capable of being vaporized upon exposure to heat under those conditions that are experienced during use of the aerosol generating pieces that are characteristic of the current disclosure; and hence are capable of yielding vapors and aerosols that are capable of being inhaled.

For aerosol delivery systems that are characterized as electronic cigarettes, the aerosol precursor most preferably incorporates tobacco or components derived from tobacco. In one regard, the tobacco may be provided as parts or pieces of tobacco, such as finely ground, milled or powdered tobacco lamina. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine).

The aerosol precursor may incorporate a so-called "aerosol former." Such materials have the ability to yield visible aerosols when vaporized upon exposure to heat under those conditions experienced during normal use of aerosol generating pieces that are characteristic of the current disclosure. Such aerosol forming materials include various polyols or polyhydric alcohols (e.g., glycerin, propylene glycol, and mixtures thereof). Many embodiments of the present disclosure incorporate aerosol precursor components that can be characterized as water, moisture or aqueous liquid. During conditions of normal use of certain aerosol generating pieces, the water incorporated within those pieces can vaporize to yield a component of the generated aerosol. As such, for purposes of the current disclosure, water that is present within the aerosol precursor may be considered to be an aerosol forming material.

It is possible to employ a wide variety of optional flavoring agents or materials that alter the sensory character or nature of the drawn mainstream aerosol generated by the aerosol delivery system of the present disclosure. For example, such optional flavoring agents may be used within the aerosol precursor to alter the flavor, aroma and organoleptic properties of the aerosol. Certain flavoring agents may be provided from sources other than tobacco. Exemplary flavoring agents may be natural or artificial in nature, and may be employed as concentrates or flavor packages.

Exemplary flavoring agents include vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, cinnamon, sandalwood, jasmine, cascarilla, cocoa, licorice, and flavorings and flavor packages of the type and character traditionally used for the flavoring of cigarette, cigar and pipe tobaccos. Syrups, such as high fructose corn syrup, also can be employed. Certain flavoring agents may be incorporated within aerosol forming materials prior to formulation of a final aerosol precursor mixture (e.g., certain water soluble flavoring agents can be incorporated within water, menthol can be incorporated within propylene glycol, and certain complex flavor packages can be incorporated within propylene glycol). Certain tobacco extracts, including nicotine, may be characterized as flavors that may be combined with one or more aerosol formers.

Aerosol precursors also may include ingredients that exhibit acidic or basic characteristics (e.g., organic acids, ammonium salts or organic amines). For example, certain organic acids (e.g., levulinic acid, succinic acid, lactic acid, and pyruvic acid) may be included in an aerosol precursor formulation incorporating nicotine, preferably in amounts up to being equimolar (based on total organic acid content) with the nicotine. For example, the aerosol precursor may include about 0.1 to about 0.5 moles of levulinic acid per one mole of nicotine, about 0.1 to about 0.5 moles of succinic acid per one mole of nicotine, about 0.1 to about 0.5 moles of lactic acid per one mole of nicotine, about 0.1 to about 0.5 moles of pyruvic acid per one mole of nicotine, or various permutations and combinations thereof, up to a concentration wherein the total amount of organic acid present is equimolar to the total amount of nicotine present in the aerosol precursor.

As one non-limiting example, a representative aerosol precursor can have the form of a mixture of about 70% to about 90% glycerin, often about 75% to about 85% glycerin; about 5% to about 20% water, often about 10% to about 15% water; about 1% to about 10% propylene glycol, often about 4% to about 8% propylene glycol; about 0.1% to about 6% nicotine, often about 1.5% to about 5% nicotine; and optional flavoring agent in an amount of up to about 6%, often about 0.1% to about 5% flavoring agent; on a weight basis. For example, a representative aerosol precursor may have the form of a formulation incorporating greater than about 76% glycerin, about 14% water, about 7% propylene glycol, about 1% to about 2% nicotine, and less than about 1% optional flavoring agent, on a weight basis. For example, a representative aerosol precursor may have the form of a formulation incorporating greater than about 75% glycerin, about 14% water, about 7% propylene glycol, about 2.5% nicotine, and less than about 1% optional flavoring agent. For example, a representative aerosol precursor may have the form of a formulation incorporating greater than about 75% glycerin, about 5% water, about 8% propylene glycol, about 6% nicotine, and less than about 6% optional flavoring agent, on a weight basis.

As another non-limiting example, a representative aerosol precursor can have the form of a mixture of about 40% to about 70% glycerin, often about 50% to about 65% glycerin; about 5% to about 20% water, often about 10% to about 15% water; about 20% to about 50% propylene glycol, often about 25% to about 45% propylene glycol; about 0.1% to about 6% nicotine, often about 1.5% to about 5% nicotine; about 0.5% to about 3%, often about 1.5% to about 2% menthol; and optional additional flavoring agent in an amount of up to about 6%, often about 0.1% to about 5% flavoring agent; on a weight basis. For example, a representative aerosol precursor may have the form of a formulation incorporating about 50% glycerin, about 11% water, about 28% propylene glycol, about 5% nicotine, about 2% menthol, and about 4% other flavoring agent, on a weight basis.

Representative types of aerosol precursor components and formulations also are set forth and characterized in U.S. Pat. No. 7,217,320 to Robinson et al. and U.S. Pat. Pub. Nos. 2013/0008457 to Zheng et al.; 2013/0213417 to Chong et al. and 2014/0060554 to Collett et al., the disclosures of which are incorporated herein by reference. Other aerosol precursors that may be employed include the aerosol precursors that have been incorporated in the VUSE® product by R. J. Reynolds Vapor Company, the BLU™ product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

The amount of aerosol precursor that is incorporated within the aerosol delivery system is such that the aerosol generating piece provides acceptable sensory and desirable performance characteristics. For example, it is highly preferred that sufficient amounts of aerosol forming material (e.g., glycerin and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. Typically, the amount of aerosol precursor incorporated within the aerosol delivery system, and particularly within the aerosol generating piece, is less than about 2 g, generally less than about 1.5 g, often less than about 1 g and frequently less than about 0.5 g.

When a plurality of reservoirs is utilized, a variety of combinations of separate components of the aerosol precursor composition may be stored in the reservoirs. In some embodiments, a substantially complete aerosol precursor composition may be stored in two or more separate reservoirs. In some embodiments, aerosol formers (e.g., glycerin, propylene glycol, and water) may be stored in one or more reservoirs and one or more flavors may be stored in one or more further reservoirs. In some embodiments, aerosol formers may be stored in one or more reservoirs, nicotine as a primary flavor may be stored in one or more further reservoirs, and optional additional flavors may be stored in one or more optional additional reservoirs (although the optional flavors may be combined with the nicotine and/or the aerosol former). Other combinations of materials stored in separate reservoirs are also encompassed, and such ability to separately store the materials can provide for precise control of aerosol composition that is provided. In particular, aerosol composition may be adjusted as desired so that liquid is only drawn from the specific reservoirs required to provide the desired aerosol composition in a specific puff on an aerosol delivery system including the microfluidic vaporizer. This ability is further described in relation to FIG. 4 below.

Returning to FIG. 3, the substrate further comprises a plurality of capillary channels 375. It is understood that one or more capillary channels 375 may be utilized to provide for delivery of the precise amount of aerosol precursor composition 367 from the reservoir 365 to the heater 355 necessary to provide the desired amount of aerosol formation. The orientation of the capillary channels 375 can vary. For example, the channels may be curved or angled rather than straight. Multiple capillary channels 375 may merge or otherwise combine in a branched effect. For example, a single capillary channel leaving the reservoir may branch into multiple capillary channels prior to or after contacting the heater. Other configurations of capillary channels that may be discerned based upon the presently described exemplary embodiments are also encompassed by this disclosure.

In FIG. 3, the capillary channels 375 are illustrated as terminating at the heat conductive layer 347. In some embodiments, the heat conductive layer 347 may be adapted for spreading of the delivered aerosol precursor composition 367 across the underlying heater 355. As such, the heat conductive layer 347 may be at least partially recessed in the substrate 345 (e.g., into the well or indentation in which the heater 355 is positioned) so that the surface of the heat conductive layer is positionally lower than the top surface 345a of the substrate. In other embodiments, the capillary channels 375 may extend at least partially across the heat conductive layer 347. In further embodiments, the heat conductive layer 347 may be absent, and the top surface 345a of the substrate 345 may extend across and over the heater 355. As such, the capillary channels 375 formed in the substrate 345 may extend at least partially across the position of the heater 355 within or below the substrate. Thus, in some embodiments, the heater can underlie at least a portion of one or more capillary channels.

The microfluidic vaporizer 330 may operate based on one or both of passive microfluidic transfer and active microfluidic transfer. Passive microfluidic transfer may rely upon surface or capillary forces to transfer the liquid through or along the capillary channels. As such, various factors (e.g., liquid viscosity, liquid density, surface tension of the liquid, contact angles in the channels, surface structure in the channels, and channel geometry) can be adjusted to achieve the level of passive transfer desired. In passive microfluidic transfer, the liquid may freely pass from the reservoir to the heater as the liquid is vaporized away from the heater.

Active microfluidic transfer may rely at least in part upon capillary forces for liquid transfer; however, external factors are also applied to direct transfer of only specific liquids in specific volumes from specific reservoirs to the heater for vaporization. Active transport elements that may be included in a microfluidic vaporizer as described herein may be, for example, selected from the group consisting of valves, pumps, heaters, electrical field formers, stimuli-responsive polymers, and combinations thereof. For example: valves may be opened and closed on command to allow liquid to flow by capillary action (or through addition of other active forces) only when desired; micropumps may be used to increase liquid flow beyond what is possible through capillary forces alone; heaters may be used to heat areas around capillary channels to provide for thermal gradients to affect liquid flow; electrical field formers may be used to establish fields that affect liquid transfer; stimuli-responsive materials (e.g., smart polymers) may be used in channel formation and/or substrate formation so that liquid transfer may be influenced by changes in the nature of the channels, such as changing the shape, conductivity, and the like of the channels in response to applied heat, electric fields, or the like.

In FIG. 3, valves 377 are shown in each of the capillary channels 375 to exemplify active transport elements that may be incorporated in the microfluidic vaporizer 330. The valves 377 may opened to allow movement of the aerosol precursor composition 367 from the reservoir 365 to the heater 355 for vaporization.

Capillary channels may be formed by a variety of methods. For example, channels may be etched or imprinted in the substrate. In other embodiments, deposition and bonding may be used to add channels to the substrate, or soft lithography techniques, such as polydimethylsiloxane (PDMS) lithography may be used. In still further embodiments, channels may be formed or added using methods such as stereolithography, photolithography, electroplating, injection molding, and embossing may be used.

A cover 385 is included with the microfluidic vaporizer 330 to overlie the substrate 345 and thus retain the aerosol precursor composition 367 within the reservoir 365 and the capillary channels 375. The cover 385 includes a plurality of microperforations 387 that preferably are sized to prevent egress of liquid but to allow passage of formed vapor therethrough. The cover 385 may be substantially in the form of a mesh. The cover 385 may be formed of any material that is heat stable and chemically non-reactive, such as any material suitable for use in forming the substrate.

The microfluidic vaporizer 330 also includes a plurality of electrical connection pins 395 and necessary electrical wiring (not shown) to allow for control of the heater 355 and any further components (e.g., valves 377) of the microfluidic vaporizer that may require such control. Any type of electrical contacts may be utilized. Preferably, the electrical connection pins 395 may be of a standard format to allow for ease of connection with a further device, such as an aerosol delivery device. Referring to FIG. 2, for example, the microfluidic vaporizer 330 of FIG. 3 may include electrical contact pins 395 in a format such that the microfluidic vaporizer may be plugged into the connection port 237. In this manner, the microfluidic vaporizer 330 may be substantially a plug and play device that is adapted for being inserted into an aerosol delivery device for aerosol formation and thereafter removed and replaced. Mating between the electrical contact pins 395 and the connection port 237 may be push/push or push/pull. In other embodiments, the microfluidic vaporizer 330 may be positioned within an aerosol delivery device in a manner wherein removal and replacement is not intended. For example, the microfluidic vaporizer may be hardwired to a control component within a housing or may be included in a shell with electrical connectors, the shell not being configured to be opened by a consumer (for example, within cartridge shell 103 in FIG. 1).

A multi-layer microfluidic vaporizer 430 is illustrated in FIG. 4. Therein, the substrate 445 is formed of a base layer 448 and an intermediate layer 446. Both layers may be formed of a material as otherwise described above. The heater 455 is attached to the base layer 448 and corresponds to a first window 446a formed in the intermediate layer 446. A heat conductive layer 447 is positioned within the first window 446a in a manner that prevents passage of liquid to the heater 455. A second window 446b is also formed in the intermediate layer 446 and forms a reservoir 465 in which an aerosol precursor composition (or a component thereof) may be stored. A plurality of capillary channels 475 are formed in the intermediate layer 446 and provide fluid connection between the first window 446a and the second window 446b. When assembled, the intermediate layer 446 contacts the base layer 448 and is sealed, glued, or otherwise connected thereto such that liquid stored in the reservoir 465 formed by the second window 446b and the base layer 448 may not seep out between the layers. A cover 485 is then applied over the intermediate layer 446 to retain a liquid aerosol precursor composition within the reservoir 465 and the capillary channels 475. Microvalves 477 are positioned within the capillary channels 475. The cover 485 includes a plurality of microperforations such that at least a portion of the cover is vapor permeable but liquid impermeable.

Yet a further embodiment of a microfluidic vaporizer 530 is illustrated in FIG. 5. As seen in the top view thereof (with an optional cover layer absent for ease of illustration), a substrate 545 is provided with a plurality of reservoirs, a single heater 555, a main capillary channel 575*a*, and a plurality of branch capillary channels 575*b* connecting a respective reservoir to the main capillary channel. As an example, reservoirs 565*a* and 565*b* can be filled with an aerosol former composition (e.g., glycerin, propylene glycol, and water), reservoir 565*c* is filled with a combination of nicotine and aerosol former carrier, reservoirs 565*d*-565*g* are each filled with different flavors, and reservoir 565*h* is filled with plain water. The use of a plurality of flavor reservoirs can allow for the use of concentrated solutions in smaller volumes. A plurality of microvalves 577 are positioned in each of the branch capillary channels 575*b*.

In use, a microfluidic vaporizer 530 as illustrated in FIG. 5 may allow for precise control of different flavor combinations. In some embodiments, when included in an aerosol delivery device, a user may use an input (see, for example, the touchscreen 209 illustrated in FIG. 2) to instruct formation of aerosol with a specific composition. For example, a user may input instruction for formation of an aerosol with a specific content of nicotine (from 0% by weight up to a predetermined threshold amount) and to include a specific additional flavor. In such example, the microfluidic vaporizer 530 would deliver aerosol former from one or both of reservoirs 565*a* and 565*b*, nicotine from reservoir 565*c*, and the requisite flavor from reservoirs 565*d*-565*g*. A single combination may be chosen for the duration of use of the aerosol delivery device (or the duration of use of the specific microfluidic vaporizer), or a different combination of flavors (including nicotine content) may be directed with each puff or any combination of puffs on an aerosol delivery device including the microfluidic vaporizer. If needed, the user may instruct the microfluidic vaporizer 530 to deliver water from reservoir 565*h* to the heater so as to clear the system of the previous flavors and/or to clean the vaporizer channels and/or heater region.

A further exemplary embodiment of a microfluidic vaporizer 630 is shown in FIG. 6. A substantially round substrate 645 is provided with a plurality of reservoirs 665*a*-665*f*, a plurality of capillary channels 675*a*-675*f*, and a heater 655. In the exemplary embodiment, reservoirs 665*a* and 665*b* can be filled with an aerosol former composition (e.g., glycerin, propylene glycol, and water), reservoir 665*c* is filled with a combination of nicotine and aerosol former carrier, and reservoirs 665*d*-665*f* are each filled with different flavors. Any combination of aerosol former, nicotine, and further flavors can be provided to the heater 655 for form an aerosol of a specifically desired composition. Active control of fluid delivery through the capillary channels 675*a*-675*f* may be achieved utilizing any method as otherwise described herein. As such, microvalves, micropumps, or the like may be included with the substrate 645.

In some embodiments, a microfluidic vaporizer can include a plurality of heaters. For example, in the embodiment of FIG. 7, a substrate 745 defines four heaters 755*a*-755*d* that are in fluid connection with four respective reservoirs 765*a*-765*d* via four respective capillary channels 775*a*-775*d*. In this embodiment, reservoir 765*a* includes a vapor former, reservoir 765*b* includes a nicotine composition, reservoir 765*c* includes a first further flavor component, and reservoir 765*d* includes a second further flavor component. In this manner, the precise quantities of vapor former, nicotine, and further flavor component can be sent to their respective heaters to form a custom vapor. Although not illustrated in FIG. 7, it is understood that one or more active transport elements (e.g., a microvalve or micropump) may be included in any manner as otherwise described herein. Through use of an input component (such as the touchscreen 209 in FIG. 2), a consumer may define the exact amount of nicotine desired in a puff on the aerosol delivery device and the exact flavor intensity desired in the puff. Moreover, as each component utilizes its own heater, possibility of cross-flavoring arising from residue on the heater from a previous, differently flavored puff can be avoided. When a plurality of heaters is utilized, the heaters may be in parallel or in series. Independent circuitry also may be utilized for two or more heaters when a plurality of heaters is used.

In the previously described exemplary embodiments, the reservoir(s), capillary channel(s), and heater(s) are all formed directly in the substrate. In further embodiments, the capillary channel(s) and the heater(s) may be defined by the substrate in that they extend outwardly from the substrate, which forms the reservoir. As such, the microfluidic vaporizer may be characterized in that one or more capillary channels extend radially from the substrate. Moreover, one or more heaters may be positioned at terminal ends of the capillary channels.

FIG. 8 illustrates an embodiment of a microfluidic vaporizer 830 wherein a substrate 845 is elongated so as to be substantially in the form of a tube. Although a tube with a circular cross-section is illustrated, the substrate may take on any desired shape. The substrate 845 is preferably hollow so as to have a chamber formed therein, the chamber being a reservoir 865 for storing an aerosol precursor composition. A plurality of heaters 855 are radially aligned around the substrate 845 and are in fluid connection with the reservoir 865 therein via a plurality of capillary channels 875. In use, aerosol precursor composition from the reservoir 865 in the substrate 845 can pass through the capillary channels 875 to the heaters 855 positioned at terminal ends of the capillary channels. The heaters 855 can include at least one wall that includes microperforations so that vapor may pass therethrough but liquid is prevented from passing therethrough.

The heaters 855 in FIG. 8 are substantially disc shaped; however, other shapes are also encompassed. The heaters may have a variety of structures that provide for the liquid aerosol precursor composition passing through the capillary channels 875 to come into a heating contact with a heating element and form vapor that may escape from the heater.

One exemplary embodiment of a heater 955 that is substantially in the form of a disc is shown in FIG. 9. Therein, the heater 955 has a floor 981 through which the capillary channel 975*a* opens. The heater floor 981 may be formed of any heat stable and chemically non-reactive material as otherwise discussed herein. A capillary coil 975*b* interconnects with the capillary channel 975a such that liquid passes from the capillary channel and through the capillary coil. Underlying the capillary coil 975b is a heating element 985, which is in a heating arrangement with the capillary coil such that the liquid in the capillary coil can be vaporized. The heating element 985 may be formed of any material as otherwise discussed herein as being suitable for providing heating. For example, a printed heating element may be utilized. In use, liquid aerosol precursor composition from a reservoir (see FIG. 8) passes through the capillary channel 975a and then is distributed through the capillary coil 975b. Upon heating of the heating element 985, the liquid in the capillary coil 975b vaporizes. A heater cover 988 may be positioned over the remaining elements of the heater 955 to retain the liquid in the capillary coil 975b until vaporization, at which time the vapor phase material may pass through the heater cover. Any cover construction that is vapor permeable and liquid impermeable may be utilized.

As another exemplary embodiment, the capillary coil 975b in FIG. 9 may be replaced with a plurality of substantially linear channel branches that extend radially from the capillary channel 975a opening through the heater floor 981. The substantially linear channel branches may open at the periphery (or rim) 990 of the heater 955 to allow for egress of formed vapor therefrom. In such embodiment, the heater cover 988 (or simply a top surface of the heater) may be solid rather than perforated. The periphery 990 of the heater 955, however, may be covered with a microperforated layer or similar material that is vapor permeable and liquid impermeable.

In embodiments such as illustrated in FIG. 8, the plurality of heaters 855 may be activated individually (e.g., one heater activation providing one puff of aerosol). Alternatively, a combination of heaters 855 may be activated substantially in unison to provide a single puff of aerosol. In further embodiments, the substrate 845 may be divided into a plurality of reservoirs, which may hold the same or different compositions. In FIG. 8, the dashed lines 866 illustrate an optional embodiment wherein the substrate 845 is divided into four reservoirs, each respective reservoir having a set of radially extending capillary channels 875 and associated heaters 855.

Yet other features, controls or components that can be incorporated into aerosol delivery systems of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. App. Pub. Nos. 2010/0163063 by Fernando et al.; 2013/0192623 to Tucker et al.; 2013/0298905 to Leven et al.; 2013/0180553 to Kim et al. and 2014/0000638 to Sebastian et al.; and U.S. patent application Ser. No. 13/840,264, filed Mar. 15, 2013, to Novak et al. and Ser. No. 13/841,233, filed Mar. 15, 2013, to DePiano et al.; which are incorporated herein by reference.

The foregoing description of use of the article can be applied to the various embodiments described herein through minor modifications, which can be apparent to the person of skill in the art in light of the further disclosure provided herein. The above description of use, however, is not intended to limit the use of the article but is provided to comply with all necessary requirements of disclosure of the present disclosure.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device comprising a shell and a microfluidic vaporizer within the shell, the microfluidic vaporizer comprising:
   a substrate;
   a reservoir formed in the substrate and configured to hold a liquid;
   a heater positioned in or on the substrate and adapted to vaporize the liquid; and
   one or more capillary channels formed in or on the substrate and configured for movement of the liquid from the reservoir to the heater.

2. The aerosol delivery device of claim 1, further comprising a cover overlying the substrate.

3. The aerosol delivery device of claim 2, wherein at least a portion of the cover is vapor permeable and liquid impermeable.

4. The aerosol delivery device of claim 1, wherein the substrate is adapted for passive transfer of the liquid from the reservoir to the heater through the one or more capillary channels.

5. The aerosol delivery device of claim 1, wherein the microfluidic vaporizer further comprises an active transport element selected from the group consisting of valves, pumps, heaters, electrical field formers, stimuli-responsive materials, and combinations thereof.

6. The aerosol delivery device of claim 1, wherein the liquid is an aerosol precursor composition, or component thereof, suitable for use in the aerosol delivery device.

7. The aerosol delivery device of any claim 1, wherein the 25 liquid comprises one or more flavors.

8. The aerosol delivery device of claim 7, wherein the one or more flavors comprises nicotine.

9. The aerosol delivery device of claim 1, wherein the liquid 5 comprises an aerosol former.

10. The aerosol delivery device of claim 9, wherein the aerosol former is selected from the group consisting of water, glycerol, propylene glycol, and combinations thereof.

11. The aerosol delivery device of claim 1, wherein the aerosol delivery device comprises a plurality of reservoirs.

12. The aerosol delivery device of claim 1, wherein the heater is a thin film.

13. The aerosol delivery device of claim 1, wherein the heater is an electrically conductive material patterned on the substrate.

14. The aerosol delivery device of claim 1, wherein the heater has a thickness of about 500 μm or less.

15. The aerosol delivery device of claim 1, wherein the heater comprises a metal or metal alloy.

16. The aerosol delivery device of claim 1, wherein the heater comprises one or more of a ceramic, carbon, a carbide, and a nitride.

17. The aerosol delivery device of claim 1, further comprising one or more electrical connections arranged on the substrate.

18. The aerosol delivery device of claim 1, wherein the substrate comprises a ceramic material.

19. The aerosol delivery device of claim 1, wherein the reservoir is a well or other indentation formed in the substrate.

20. The aerosol delivery device of claim 1, wherein the heater is arranged on a flat surface of the substrate.

21. The aerosol delivery device of claim 1, wherein the heater is positioned at terminals ends of the one or more capillary channels.

* * * * *